(12) United States Patent
Furukawa et al.

(10) Patent No.: US 8,198,475 B2
(45) Date of Patent: Jun. 12, 2012

(54) METHOD FOR PRODUCING ADAMANTYL (METH)ACRYLATES

(75) Inventors: Kikuo Furukawa, Katsushika-ku (JP); Yoshihisa Arai, Katsushika-ku (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 335 days.

(21) Appl. No.: 12/639,530

(22) Filed: Dec. 16, 2009

(65) Prior Publication Data

US 2010/0168464 A1 Jul. 1, 2010

(30) Foreign Application Priority Data

Dec. 26, 2008 (JP) ................................. 2008-332866

(51) Int. Cl.
*C07C 67/48* (2006.01)
*C07C 67/58* (2006.01)
*C07C 69/54* (2006.01)

(52) U.S. Cl. ......................................... 560/220; 560/218
(58) Field of Classification Search .................. None
See application file for complete search history.

(56) References Cited

FOREIGN PATENT DOCUMENTS

| JP | 1-53633 B2 | 11/1989 |
|----|----|----|
| JP | 04-039665 A | 2/1992 |
| JP | 06-305044 A | 11/1994 |
| JP | 2006-016379 A | 1/2006 |

*Primary Examiner* — Yevegeny Valenrod
(74) *Attorney, Agent, or Firm* — Sughrue Mion, PLLC

(57) ABSTRACT

The present invention provides an efficient production method suitable to industrial-scale production not requiring column purification for adamantyl (meth)acrylates having an adamantine skeleton having utility in crosslinked resins, optical fibers, optical waveguides, optical disc substrates and other optical materials.

6 Claims, No Drawings

METHOD FOR PRODUCING ADAMANTYL (METH)ACRYLATES

BACKGROUND OF THE INVENTION

1. Field of the Invention

The present invention relates to a method for producing adamantyl (meth)acrylates having an adamantane skeleton, which are excellent in optical properties, heat resistance and acid dissociability and useful for crosslinked resins, optical fibers, optical waveguides, optical disc substrates, other optical materials such as photoresists and their starting materials, as well as for intermediates for medicines and agrochemical intermediates, and other various industrial products, etc.

2. Description of the Related Art

Adamantane has a rigid structure of high symmetricity and its derivatives show specific functions, and therefore, they are known to be useful for high-function resin materials, medicine intermediates, optical materials (see JP-B 1-53633 and JP-A 6-305044), photoresists (see JP-A 4-39665 and JP-A 2006-016379), etc.

BRIEF SUMMARY OF THE INVENTION

Of those adamantanes described in the above-mentioned patent publications, the adamantane derivatives described in JP-A 2006-016379 are obtained generally through (meth)acryl-esterification of the starting compound of adamantane-dialcohols. However, the present inventors have found the following problems with the method for producing adamantane derivatives described in the patent publication. Concretely, according to the method for producing adamantane derivatives described in the patent publication, the reaction product is a mixture of the starting compound, monoester and diester, and therefore, it is not easy to separate and purify the mixture. For the separation and purification, for example, employable is a method based on adsorption such as silica gel column purification, or any other known method of distillation, crystallization, etc.; however, industrial use of these methods is difficult because of the following reasons.

First, column purification may readily enable separation and purification, but in industrial-scale production, it has some disadvantages in that the production volume is small and the production cost is high. Regarding distillation purification, it is difficult to vaporize the compound by itself in an industrial-scale distillation method since the boiling point of the compound is high. Accordingly, crystallization could be only one industrially practicable purification method, which, however, is intrinsically problematic in that the crystallization is extremely difficult when the purity of the objective compound is low. Therefore, the intended compound must be sufficiently separated from the by-products before it is collected through crystallization. For these reasons, it is necessary to establish a production method suitable to industrial-scale production.

An object of the present invention is to provide an efficient production method suitable to industrial-scale production not requiring column purification for adamantyl (meth)acrylates having an adamantane skeleton and useful as monomers for use for resins excellent in optical properties, etc.

The present inventors have assiduously studied for the purpose of solving the above-mentioned problems and, as a result, have found that a mixture of compounds of formulae (2) to (4) can be efficiently separated according to the present invention mentioned below.

Specifically, the present invention is a method for producing adamantyl (meth)acrylates of formulae (3) and (4), comprising a reaction step of reacting a compound of formula (1) with a (meth)acryloyl halide or a (meth)acrylic anhydride in a reaction solution to give a mixture of compounds of formulae (2) to (4), and a separation step of separating the mixture of compounds of formulae (2) to (4); wherein the separation step comprises an extraction step of extracting compounds of formulae (2) and (3) from the reaction solution with a mixed solvent of water and a polar organic solvent, thereby giving a water/polar organic solvent solution containing the compounds of formulae (2) and (3) and the mixed solvent, and a back-extraction step of back-extracting the compound of formula (3) from the water/polar organic solvent solution with a non-polar organic solvent,

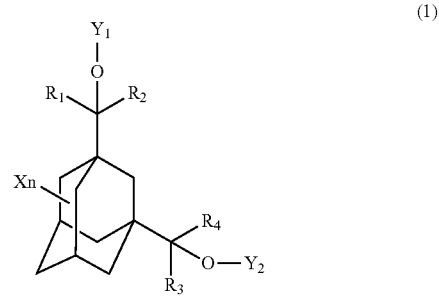

wherein X's are the same or different, each representing a hydrogen atom, an alkyl group, a halogen-containing alkyl group, a halogen group, a nitrile group, or an ether group; n indicates an integer of 14; $R_1$ to $R_4$ are the same or different, each representing an alkyl group or a halogen-containing alkyl group; and $Y_1$ and $Y_2$ are the same or different, each representing a hydrogen atom, lithium, sodium, or a magnesium halide group,

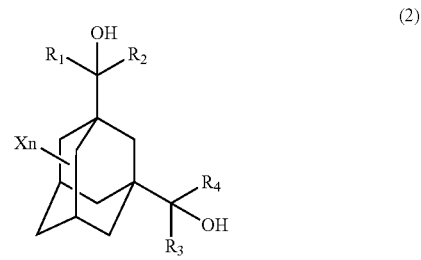

wherein X's are the same or different, each representing a hydrogen atom, an alkyl group, a halogen-containing alkyl group, a halogen group, a nitrile group, or an ether group; n indicates an integer of 14; and $R_1$ to $R_4$ are the same or different, each representing an alkyl group or a halogen-containing alkyl group,

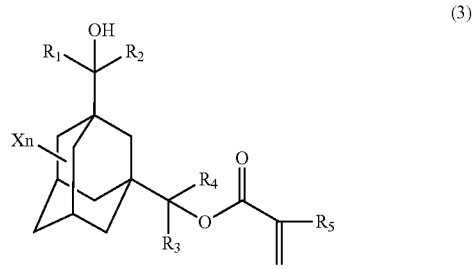

wherein X's are the same or different, each representing a hydrogen atom, an alkyl group, a halogen-containing alkyl group, a halogen group, a nitrile group, or an ether group; n indicates an integer of 1-4; $R_1$ to $R_4$ are the same or different, each representing an alkyl group or a halogen-containing alkyl group; and $R_5$ represents a hydrogen atom or a methyl group, (4)

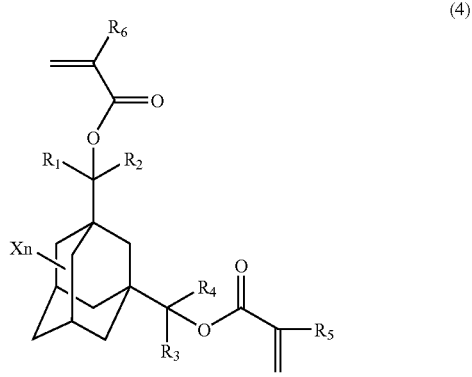

wherein X's are the same or different, each representing a hydrogen atom, an alkyl group, a halogen-containing alkyl group, a halogen group, a nitrile group, or an ether group; n indicates an integer of 1-4; $R_1$ to $R_4$ are the same or different, each representing an alkyl group or a halogen-containing alkyl group; and $R_5$ and $R_6$ are the same or different, each representing a hydrogen atom or a methyl group.

The compounds of formulae (3) and (4) in the present invention and functional resin compositions starting from them have a hydrophobic alicyclic skeleton and are used for crosslinked resins, optical fibers, optical waveguides, optical disc substrates, other optical materials such as photoresists and their starting materials, and also for intermediates for medicines and agrochemical intermediates, and other various industrial products, etc. In particular, they have an acid-dissociable ester group and undergo large polarity change before and after dissociation at the acid-dissociable group thereof, therefore having a large dissolution contrast; and accordingly, they are useful as monomers for photoresists for KrF excimer laser, ArF excimer laser or $F_2$ excimer laser, or X-ray, EUV or electron-beam lithography. Above all, when incorporated in conventional ArF resist polymers, they enhance the contrast in microfabrication.

According to the present invention, there is provided an efficient production method suitable to industrial-scale production for adamantyl (meth)acrylates having an adamantane skeleton, excellent in optical properties, heat resistance and acid dissociability and useful for crosslinked resins, optical fibers, optical waveguides, optical disc substrates, other optical materials such as photoresists and their starting materials, as well as for intermediates for medicines and agrochemical intermediates, and various industrial products, etc.

DETAILED DESCRIPTION OF THE INVENTION

Hereinafter embodiments of the present invention will be described.

The present invention is a method of producing adamantyl (meth)acrylates of formulae (3) and (4), which comprises a reaction step of reacting a compound of formula (1) with a (meth)acryloyl halide or a (meth)acrylic anhydride in a reaction solution to give a mixture of compounds of formulae (2) to (4), and a separation step of separating the mixture of compounds of formulae (2) to (4). The separation step comprises an extraction step of extracting compounds of formulae (2) and (3) from the reaction solution with a mixed solvent of water and a polar organic solvent, thereby giving a water/polar organic solvent solution containing the compounds of formulae (2) and (3) and the mixed solvent, and a back-extraction step of back-extracting the compound of formula (3) from the water/polar organic solvent solution with a non-polar organic solvent.

The individual steps will be described in detail below.

[Reaction Step]

The reaction step is a step of reacting a compound of formula (1) with a (meth)acryloyl halide or a (meth)acrylic anhydride in a reaction solution to give a mixture of compounds of formulae (2) to (4). Specifically, a mixture of compounds of formulae (2) to (4) is produced in the reaction solution through esterification of an adamantane compound of formula (1) with a (meth)acrylic acid compound.

(1)

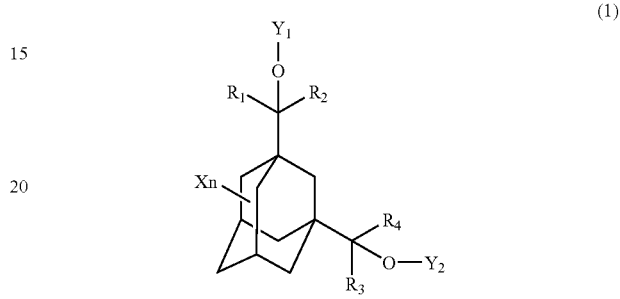

wherein X's are the same or different, each representing a hydrogen atom, an alkyl group, a halogen-containing alkyl group, a halogen group, a nitrile group, or an ether group; n indicates an integer of 1-4; $R_1$ to $R_4$ are the same or different, each representing an alkyl group or a halogen-containing alkyl group; and $Y_1$ and $Y_2$ are the same or different, each representing a hydrogen atom, lithium, sodium, or a magnesium halide group, (2)

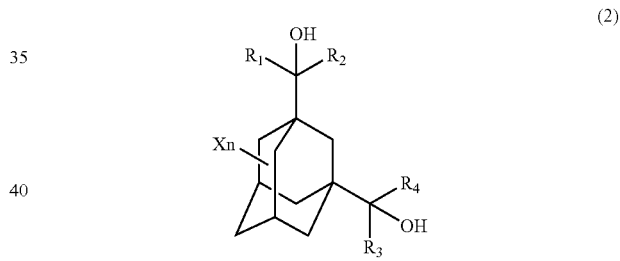

wherein X's are the same or different, each representing a hydrogen atom, an alkyl group, a halogen-containing alkyl group, a halogen group, a nitrile group, or an ether group; n indicates an integer of 1-4; and $R_1$ to $R_4$ are the same or different, each representing an alkyl group or a halogen-containing alkyl group, (3)

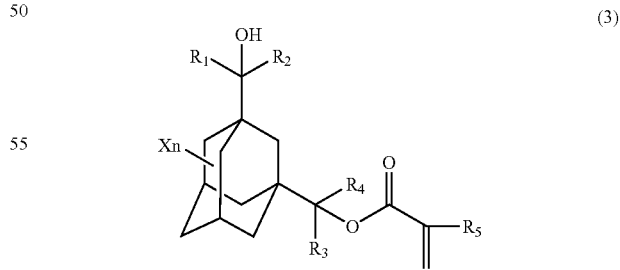

wherein X's are the same or different, each representing a hydrogen atom, an alkyl group, a halogen-containing alkyl group, a halogen group, a nitrile group, or an ether group; n indicates an integer of 1-4; $R_1$ to $R_4$ are the same or different, each representing an alkyl group or a halogen-containing alkyl group; and $R_5$ represents a hydrogen atom or a methyl group,

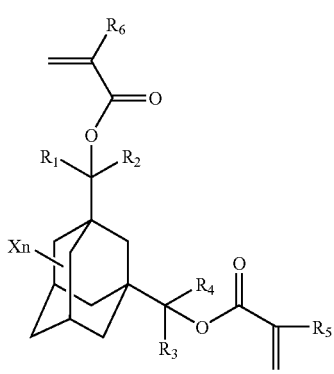

(4)

wherein X's are the same or different, each representing a hydrogen atom, an alkyl group, a halogen-containing alkyl group, a halogen group, a nitrile group, or an ether group; n indicates an integer of 14; $R_1$ to $R_4$ are the same or different, each representing an alkyl group or a halogen-containing alkyl group; and $R_5$ and $R_6$ are the same or different, each representing a hydrogen atom or a methyl group.

The reaction solution mainly contains an adamantane compound of formula (1), a (meth)acryloyl halide and/or a (meth) acrylic anhydride, and a solvent for their reaction.

The adamantane compound of formula (1) for use herein is generally a compound having two hydroxyl groups. The compound having two hydroxyl groups is represented by formula (1) where $Y_1$ and $Y_2$ are both hydrogen atoms. The hydroxyl group may be alcoholated with an alkali metal such as lithium or sodium, or an alkyl lithium such as butyllithium, or a Grignard reagent such as ethylmagnesium bromide or the like; and thereafter the resulting compound may be esterified with a (meth)acrylic acid compound. The alcoholate compound is represented by formula (1) wherein $Y_1$ and $Y_2$ are the same or different, each representing Li, Na, MgBr, MgCl, MgI, etc.

A compound produced through reaction of a 1,3-adamantane-dicarboxylic acid and an organic metal compound may also have a form of the above-mentioned alcoholate compound, and the compound of the type may be esterified directly with a (meth)acrylic acid compound.

A (meth)acrylic acid compound includes, for example, (meth)acryloyl halides, (meth)acrylic anhydrides, (meth)acrylic acids, (meth)acrylates, etc.; and in the present invention, used are a (meth)acryloyl halide and a (meth)acrylic anhydride or any one of these (hereinafter referred to as "(meth)acrylic acid compound", if desired), as capable of producing compounds of formulae (3) and (4) at a high reaction yield. Concretely, the (meth)acryloyl halide includes acryloyl chloride and methacryloyl chloride. The (meth) acrylic anhydride includes methacrylic anhydride, acrylic anhydride, and methacrylic/acrylic anhydride. The amount of the (meth)acrylic acid compound may be from 0.5 to 10 equivalents relative to the adamantane compound of formula (1) (hereinafter this may be referred to as a starting compound), preferably from 0.7 to 3 equivalents (in this, one equivalent corresponds to the necessary acryloyloxy group). When the amount of the (meth)acrylic acid compound to be used is less than 0.5 equivalents, then the yield may lower; but when more than 10 equivalents, it is uneconomical.

For rapidly reacting the adamantane compound of formula (1) with the (meth)acrylic acid compound at a high yield, a base compound is preferably added to the starting compound. Adding the base compound promotes the reaction, therefore giving the intended substance at a higher yield. The base compound to be added is preferably an amine compound, as capable of giving compounds of formulae (3) and (4) at a high reaction yield. Examples of the amine compound include aliphatic amines such as methylamine, dimethylamine, trimethylamine, ethylamine, diethylamine, triethylamine, n-propylamine, di-n-propylamine, di-iso-propylamine, tri-n-propylamine, n-butylamine, di-n-butylamine, di-iso-butylamine, tri-n-butylamine, diphenylamine, 1,5-diazabicyclo[4.3.0]nonene-5,1,5-diazabicyclo[5.4.0]undecene-5, diazabicyclo[2.2.2]octane; anilines such as aniline, methylaniline, dimethylaniline, toluidine, anisidine, chloroaniline, bromoaniline, nitroaniline, aminobenzoic acid; nitrogen-containing heterocyclic compounds such as pyridines, e.g., pyridine, dimethylaminopyridine, and pyrroles, quinolines, piperidines, etc.

As the base compound, also usable are metal alkoxides such as sodium methoxide, lithium methoxide; quaternary ammonium hydroxides such as tetramethylammonium hydroxide, trimethyl-n-propylammonium hydroxide; amine sulfates, nitrates and chlorides such as ethylammonium sulfate, trimethylammonium nitrate, anilinium chloride; inorganic bases such as sodium hydrogencarbonate; Grignard reagents such as ethylmagnesium bromide, in addition to the above-mentioned amine compounds.

Preferably, the amount of the base compound to be used is at most 10 equivalents relative to the starting compound. Even though the amount of the base compound used is more than 10 equivalents, the effect of the base compound added is no more enhanced. However, in case where the base compound is liquid, the compound itself may serve also as a solvent and therefore the amount of the base compound to be used is not limited. The method of adding the base compound is not specifically limited. The base compound may be previously fed into the reactor before a (meth)acrylic acid compound is put thereinto, or it may be fed into the reactor after a (meth)acrylic acid compound is put thereinto. The compound may be dropwise put into the reactor simultaneously with a (meth)acrylic acid compound thereinto. In this case, the system is preferably so controlled as to prevent the reaction temperature from rising abnormally, as capable of retarding the promotion of side reactions.

The solvent to be used in reacting the adamantane compound of formula (1) and a (meth)acrylic acid compound is preferably one in which the solubility of the starting compound and the intended product (adamantyl (meth)acrylates) is high. The solvent includes halogen compounds such as dichloromethane, chloroform, 1,2-dichloroethane; ether compounds such as tetrahydrofuran, diethyl ether, diisopropyl ether, di-n-propyl ether, di-n-butyl ether, methyl t-butyl ether, dioxane; aromatic compounds such as benzene, toluene, xylene, ethylbenzene, cumene, mesitylene, pseudocumene; aliphatic hydrocarbons having from 6 to 10 carbon atoms such as hexane, heptane, octane, nonane, decane; alicyclic hydrocarbons having from 6 to 10 carbon atoms such as cyclohexane, methylcyclohexane, dimethylcyclohexane, ethylcyclohexane; nitrile compounds such as acetonitrile, benzonitrile; ester compounds such as ethyl formate, methyl formate, methyl acetate, ethyl acetate, butyl acetate, methyl propionate, ethyl propionate, propyl propionate; amides such as formamide, acetamide, dimethylformamide, dimethylacetamide, etc. The above-mentioned base compound may serve also as a solvent. One or more of those solvents may be used herein either singly or as a mixed system thereof. The amount of the solvent to be used may be in a ratio of from 0.1 to 20 parts by weight relative to 1 part by weight of the starting compound, preferably from 1 to 10 parts by weight.

The reaction temperature may be generally from −70° C. to 200° C., preferably from −50° C. to 80° C. When the reaction temperature is lower than −70° C., then the reaction speed may be low; but when higher than 200° C., then the reaction may be difficult to control or side reactions may go on to lower the yield. The reaction time for esterification in the present invention may be generally from 0.5 to 1000 hours, preferably from 1 to 100 hours. However, the reaction time depends on the reaction temperature and the esterification method, and is therefore determined in accordance with the intended yield; and accordingly, the reaction time is not limited to the above range.

In esterification reaction, a polymerization inhibitor may be added to the system. Not specifically limited, the polymerization inhibitor may be any ordinary one, including, for example, nitroso compounds such as 2,2,6,6-tetramethyl-4-hydroxypiperidin-1-oxyl, N-nitrosophenylhydroxylamine ammonium salt, N-nitrosophenylhydroxylamine aluminium salt, N-nitroso-N-(1-naphthyl)hydroxylamine ammonium salt, N-nitrosodiphenylamine, N-nitroso-N-methylaniline, nitrosonaphthol, p-nitrosophenol, N,N'-dimethyl-p-nitrosoaniline; sulfur-containing compounds such as phenothiazine, methylene blue, 2-mercaptobenzimidazole; amines such as N,N'-diphenyl-p-phenylenediamine, N-phenyl-N'-isopropyl-p-phenylenediamine, 4-hydroxydiphenylamine, aminophenol; quinones such as hydroxyquinoline, hydroquinone, methylhydroquinone, p-benzoquinone, hydroquinone monomethyl ether; phenols such as methoxyphenol, 2,4-dimethyl-6-t-butylphenol, catechol, 3-S-butyl-catechol, 2,2-methylenebis-(6-t-butyl-4-methylphenol); imides such as N-hydroxyphthalimide; oximes such as cyclohexane oxime, p-quinone dioxime; dialkylthio dipropionates, etc. The amount of the polymerization inhibitor to be added may be from 0.001 part by weight to 10 parts by weight relative to 100 parts by weight of the (meth)acrylic acid compound, preferably from 0.01 part by weight to 1 part by weight.

After the reaction, the reaction liquid is washed with water to remove excessive (meth)acrylic acid compounds and additives such as acid and base. In this stage, the washing water may contain a suitable inorganic salt such as sodium chloride, sodium hydrogencarbonate, etc. The unreacted (meth)acrylic acid compounds are removed through washing with alkali. For the alkali washing, usable is an aqueous sodium hydroxide solution, a potassium hydroxide solution, aqueous ammonia or the like; but the alkali ingredient in the solution to be used is not specifically limited. For removing base and metal impurities, acid washing may be performed. For the acid washing, usable is an inorganic acid such as an aqueous hydrochloric acid solution, an aqueous sulfuric acid solution or an aqueous phosphoric acid solution, or an organic acid such as an aqueous oxalic acid solution, etc. In washing, an organic solvent may be added to the reaction solution, depending on the physical properties of the compounds of formulae (2) to (4). The organic solvent to be added may be the same as that used in the above-mentioned esterification reaction, or may be a different solvent.

Depending on the physical properties of the compound of formula (2), the compound may partly precipitate after the reaction or after the washing. In case where the compound precipitates after the reaction, the precipitate may be separated through filtration. Alternatively, a solvent capable of dissolving the compound of formula (2) may be added to the system and the washing treatment may be continued further. In case where the compound precipitates after the washing, the compound of formula (2) may be separated through filtration, or may be dissolved in the solvent used in the extraction step to be mentioned later.

[Separation Step]

The separation step is a step of separating a mixture of the compounds of formulae (2) to (4). The separation step comprises the following extraction step and back-extraction step.

(Extraction Step)

The organic layer after the washing contains a mixture of the compounds of formulae (2) to (4). First, the compounds of formulae (2) and (3) are separated from the compound of formula (4) through solvent extraction. As the solvent for extraction, used is a water/polar organic solvent. The water/polar organic solvent means a mixed solvent of water and a polar organic solvent. When such a water/polar organic solvent is used, then the compounds of formulae (2) and (3) are extracted into the water/polar organic solvent, thereby giving a water/polar organic solvent solution containing the compounds of formulae (2) and (3) and the water/polar organic solvent. On the other hand, the compound of formula (4) is kept remaining in the organic layer.

Depending on the type of the solvent that dilutes the organic layer containing the compounds of formulae (2) to (4), the intended compounds could not be extracted into the water/polar organic solvent. In such a case, it is desirable to remove the solvent that has previously diluted the compounds, according to a known method of distillation or the like. Preferably, the polar organic solvent is an aliphatic alcohol having from 1 to 3 carbon atoms, or acetonitrile. In this case, the solution may be separated more readily from the organic layer through liquid-liquid separation, than in a case where the polar organic solvent has 4 or more carbon atoms. The diluent solvent is preferably any of aliphatic hydrocarbons or cycloaliphatic hydrocarbons having from 6 to 10 carbon atoms, or aromatic compounds such as benzene, toluene, xylene, ethylbenzene, cumene, mesitylene, pseudocumene or the like, as facilitating the liquid-liquid separation from the water/polar organic solvent.

The water/polar organic solvent for use herein may be prepared generally by mixing them in a ratio of from 2 to 10 times by weight of a polar organic solvent relative to the basis amount, 1, of water, preferably from 3 to 7 times by weight. In this case, the extraction efficiency for the compounds of formulae (2) and (3) increases more than in a case where the ratio of the polar organic solvent is less than 2 times by weight. In addition, as compared with a case where the ratio of the polar organic solvent is more than 10 times by weight, the present case is more favorable in that the extraction of the compound of formula (4) is well inhibited and that the failure in liquid-liquid separation of the reaction solution is also well inhibited. The amount of the water/polar organic solvent to be used may be from 0.2 to 10 times by weight relative to the basis amount, 1, of the solution containing the compounds of formulae (2) to (4), preferably from 0.5 to 4 times by weight, more preferably from 0.8 to 2 times by weight. When the amount of the water/polar organic solvent to be used is within the above range, then the extraction efficiency is enhanced more than in a case where the amount is less than 0.2 time by weight, and in addition, the compound of formula (4) is prevented more sufficiently from being extracted into the water/polar organic solvent than in a case where the amount of the water/polar organic solvent to be used is more than 10 times by weight. The extraction frequency is not specifically limited, as depending on the extraction efficiency; but in general, the extraction may be once to 6 times.

After processed for extraction with the water/polar organic solvent, the organic layer contains the compound of formula (4) at high purity. The organic layer is processed for separation through treatment with activated carbon, filtration, concentration, crystallization or the like, or through a combination of those treatments, whereby the compound of formula (4) may be readily separated and purified.

(Back-Extraction Step)

Next, from the water/polar organic solvent solution containing a mixture of the compounds of formulae (2) and (3) and a water/polar organic solvent, the compounds of formulae (2) and (3) are separated through solvent extraction. Specifically, a non-polar organic solvent is added to the water/polar organic solvent solution to thereby back-extract the compound of formula (3) into the non-polar organic solvent while the compound of formula (2) is kept remaining in the water/polar organic solvent solution. As the non-polar organic solvent, preferred are aliphatic hydrocarbons or cycloaliphatic hydrocarbons having from 6 to 10 carbon atoms, alkylbenzenes such as toluene, xylene, ethylbenzene, cumene, mesitylene, pseudocumene, or aromatic compounds such as benzene, as capable of attaining good liquid-liquid separation from the water/polar organic solvent.

In the present back-extraction step, the polarity of the water/polar organic solvent may be changed by adding water or by removing the polar organic solvent through evaporation. Applying this operation may better the separability of the compounds of formulae (2) and (3).

The amount of the non-polar organic solvent to be used may be generally from 0.2 to 10 times by weight relative to the basis amount, 1, of the water/polar organic solvent solution containing a mixture of the compounds of formulae (2) and (3), preferably from 0.5 to 4 times by weight, more preferably from 0.8 to 2 times by weight. In this case, the back-extraction efficiency is better than in a case where the amount of the non-polar organic solvent to be used for back extraction is less than 0.2 times by weight; and the reactor-base yield is higher than in a case where the amount of the non-polar organic solvent to be used for back extraction is more than 10 times by weight. The extraction frequency is not specifically limited, as depending on the extraction efficiency; but in general, the extraction may be once to 4 times.

The back-extracted non-polar organic solvent contains the compound of formula (3) at high purity. The organic layer is processed for separation through treatment with activated carbon, filtration, concentration, crystallization or the like, or through a combination of those treatments, whereby the compound of formula (3) may be readily separated and purified.

After the back extraction, the water/polar organic solvent contains the compound of formula (2) at high purity. The water/polar organic solvent layer is processed for separation through treatment with activated carbon, filtration, concentration, crystallization or the like, or through a combination of those treatments, whereby the compound of formula (2) may be readily separated and purified.

In the manner as above, adamantyl (meth)acrylates of formula (4) and adamantyl (meth)acrylates of formula (3) are obtained. According to the production method of the present invention, adamantyl (meth)acrylates of formulae (3) and (4) can be separated efficiently, not requiring column purification. Accordingly, the production method of the present invention is suitable for industrial-scale production.

Hereinafter the contents of the present invention will be described more concretely with reference to Examples and Comparative Examples. However, the present invention should not be restricted at all by the following Examples.

Example 1

126 g of 1,3-adamantane-diisopropanol and 1000 ml, of 1,2-dichloroethane were fed into a 5-neck flask equipped with a stirrer, a thermometer, a Dimroth condenser and two dropping funnels; and 105 g of methacryloyl chloride and 151 g of triethylamine were simultaneously dropwise added thereto, taking 1 hour. Next, the reaction solution in the 5-neck flask was stirred at 59 to 65° C. for 4 hours, then the reaction solution was cooled to room temperature, and thereafter 100 mL of water was added thereto to stop the reaction. Since the unreacted starting compound partly precipitated therein, the reaction solution was filtered under suction through a 5C paper filter and separated into the unreacted starting compound and a filtrate. In this stage, the amount of the unreacted starting compound was 25 g. The filtrate was separated into an organic layer and an aqueous layer. Next, the organic layer was washed with 800 g of aqueous 5% sodium hydroxide solution, 250 mL of ion-exchanged water, 750 g of aqueous 10% sulfuric acid solution, 250 mL of ion-exchanged water, and 250 mL of ion-exchanged water in that order, and then concentrated to give 138 g of a crude product. 320 mL of hexane was added to the thus-obtained crude product, and the unreacted starting compound precipitated. The crude product was filtered under suction through a 50 paper filter, thereby giving 15 g of the unreacted starting compound and a hexane solution.

64 mL of water and 320 mL of methanol were added to the obtained hexane solution, and well stirred, and the resulting liquid was separated into a hexane solution and a water/methanol solution through liquid-liquid separation. This operation was thereafter repeated further three times.

1374 g of the water/methanol solution was concentrated to 565 g. 640 mL of heptane was added to the thus-concentrated water/methanol solution, well stirred, and the resulting liquid was separated into a heptane solution and a water/methanol solution through liquid-liquid separation. Further, 640 mL of heptane was added to the concentrated water/methanol solution, well stirred, and the resulting liquid was separated into a heptane solution and a water/methanol solution through liquid-liquid separation. All the heptane solutions collected in the above liquid-liquid separation were mixed, then 12 g of activated carbon was added thereto and stirred for 1 hour, and thereafter this was filtered through a 5C paper filter and a membrane filter (pore size: 0.1 μm). The heptane layer thus recovered in the filtrate was concentrated and stirred at 0° C. for 1 hour, thereby giving 43 g of 2-methacryloyloxy-2-(3-(2-hydroxy-2-propyl)-1-adamantyl)propane (monomethacrylate of the starting compound).

On the other hand, the hexane solution after the extraction was concentrated, then methanol was added thereto, and this was cooled to 0° C. to give 4 g of 2-methacryloyloxy-2-(3-(2-methacryloyloxy-2-propyl)-1-adamantyl)propane (dimethacrylate of the starting compound).

Example 2

25 g of 1,3-adamantane-diisopropanol, 50 mL of tetrahydrofuran, 70.5 g of pyridine and 0.0986 g of phenothiazine were fed into a 4-neck flask equipped with a stirrer, a thermometer, a Dimroth condenser and a dropping funnel, and heated to 50° C. 10.3 g of methacryloyl chloride was dropwise added thereto, taking 15 minutes. Next, the reaction solution was stirred for 4 hours while kept at 50° C. Next, the reaction solution was cooled with ice, then 50 mL of ion-exchanged water was dropwise added thereto, and this was poured into 500 g of aqueous 10% sulfuric acid solution. Further, 100 mL of heptane, 30 g of sodium chloride and 250 mL of tetrahydrofuran were added to the aqueous 10% sulfuric acid solution, then well stirred, and thereafter the resulting liquid was processed for liquid-liquid separation into an organic layer and an aqueous layer. The organic layer was washed with 250 mL of ion-exchanged water, 100 g of aqueous 5% sodium hydroxide solution, and 250 ml, of ion-exchanged water in that order. 235 g of the organic layer was concentrated under reduced pressure to 68 g, then 100 mL of heptane was added thereto, and this was re-concentrated to 117 g. The organic layer was cooled with ice for 2 hours, and the organic layer with the starting compound precipitated therein was filtered under suction through a 5C paper filter, and separated into the precipitated starting compound and a filtrate.

The precipitated starting compound was rinsed with 100 mL of heptane. The recovery yield of the collected starting compound was 35%. On the other hand, the filtrate was analyzed through HPLC, which confirmed the existence of the starting compound, the monoester and the diester in the filtrate, in an yield ratio by mol of starting compound/monoester/diester=2/38/4 (based on the starting compound fed in the reactor). The filtrate was extracted four times with methanol (50 mL)/ion-exchanged water (10 mL). Through this operation, the starting compound and the monoester were separated from the diester. The methanol/ion-exchanged water solution was concentrated to 211 g, and extracted twice with 150 mL of heptane. Through this operation, the starting compound and the monoester were separated from each other. The heptane layer obtained in this stage was analyzed through HPLC, which confirmed the existence of the starting compound, the monoester and the diester in the heptane layer, in a mole yield of starting compound/monoester/diester 0.4/27/0.3 (based on the starting compound fed in the reactor). The heptane layer was concentrated under reduced pressure to 23 g, and a seed crystal of the monoester of the starting compound was added to the heptane layer, which gave a crystal therein. The heptane layer was further cooled with ice for 2 hours, and then filtered under suction through a 5C paper filter thereby giving 7.4 g of 2-methacryloyloxy-2-(3-(2-hydroxy-2-propyl)-1-adamantyl)propane (monomethacrylate of the starting compound).

On the other hand, the filtrate after the extraction with methanol/ion-exchanged water was concentrated, then methanol was added thereto, and this was cooled to 0° C. to give 2-methacryloyloxy-2-(3-(2-methacryloyloxy-2-propyl)-1-adamantyl)propane (dimethacrylate of the starting compound).

What is claimed is:
1. A method for producing adamantyl (meth)acrylates of formulae (3) and (4), comprising
a reaction step of reacting a compound of formula (1) with a (meth)acryloyl halide or a (meth)acrylic anhydride in a reaction solution to give a mixture of compounds of formulae (2) to (4), and
a separation step of separating the mixture of compounds of formulae (2) to (4);
wherein the separation step comprises an extraction step of extracting compounds of formulae (2) and (3) from the reaction solution with a mixed solvent of water and a polar organic solvent, thereby giving a water/polar organic solvent solution containing the compounds of formulae (2) and (3) and the mixed solvent, and a back-extraction step of back-extracting the compound of formula (3) from the water/polar organic solvent solution with a non-polar organic solvent:

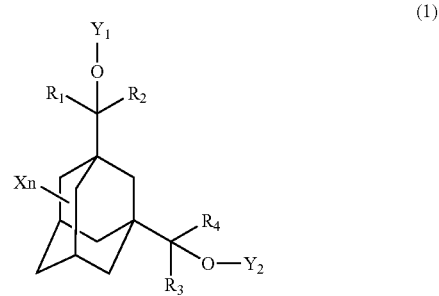

(1)

wherein X's are the same or different, each representing a hydrogen atom, an alkyl group, a halogen-containing alkyl group, a halogen group, a nitrile group, or an ether group; n indicates an integer of 1-4; $R_1$ to $R_4$ are the same or different, each representing an alkyl group or a halogen-containing alkyl group; and $Y_1$ and $Y_2$ are the same or different, each representing a hydrogen atom, lithium, sodium, or a magnesium halide group,

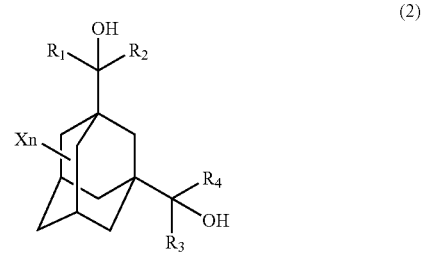

(2)

wherein X's are the same or different, each representing a hydrogen atom, an alkyl group, a halogen-containing alkyl group, a halogen group, a nitrile group, or an ether group; n indicates an integer of 1-4; and $R_1$ to $R_4$ are the same or different, each representing an alkyl group or a halogen-containing alkyl group,

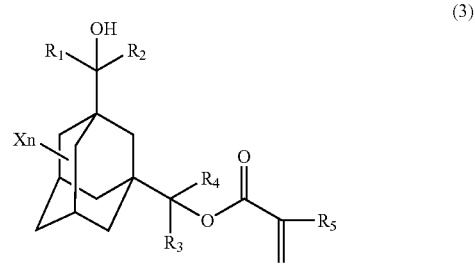

(3)

wherein X's are the same or different, each representing a hydrogen atom, an alkyl group, a halogen-containing alkyl group, a halogen group, a nitrile group, or an ether group; n indicates an integer of 1-4; $R_1$ to $R_4$ are the same or different, each representing an alkyl group or a halogen-containing alkyl group; and $R_5$ represents a hydrogen atom or a methyl group,

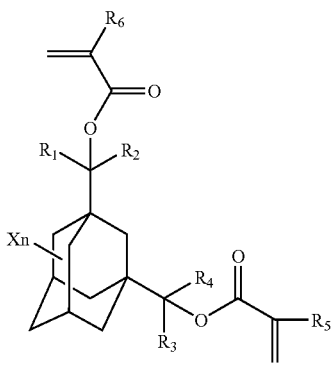

(4)

wherein X's are the same or different, each representing a hydrogen atom, an alkyl group, a halogen-containing alkyl group, a halogen group, a nitrile group, or an ether group; n indicates an integer of 1-4; $R_1$ to $R_4$ are the same or different, each representing an alkyl group or a halogen-containing alkyl group; and $R_5$ and $R_6$ are the same or different, each representing a hydrogen atom or a methyl group.

2. The method as claimed in claim 1, wherein the (meth)acrylic acid compound is added in a ratio of from 0.5 to 10 equivalents relative to the adamantane compound of formula (1).

3. The method as claimed in claim 1, wherein the polar organic solvent is an aliphatic alcohol compound having from 1 to 3 carbon atoms or an acetonitrile.

4. The method as claimed in claim 1, wherein the non-polar organic solvent is a benzene or an alkylbenzene, or an aliphatic hydrocarbon compound or a cycloaliphatic hydrocarbon compound having from 6 to 10 carbon atoms.

5. The method as claimed in claim 1, wherein the compound of formula (1) is reacted with the (meth)acrylic acid compound in the presence of a base compound.

6. The method as claimed in claim 5, wherein the base compound is an amine compound.

* * * * *